US008612020B2

(12) United States Patent
Donofrio

(10) Patent No.: US 8,612,020 B2
(45) Date of Patent: Dec. 17, 2013

(54) IMPLANTABLE THERAPEUTIC NERVE STIMULATOR

(75) Inventor: William T. Donofrio, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 517 days.

(21) Appl. No.: 12/570,774

(22) Filed: Sep. 30, 2009

(65) Prior Publication Data
US 2010/0114260 A1 May 6, 2010

Related U.S. Application Data

(60) Provisional application No. 61/110,300, filed on Oct. 31, 2008, provisional application No. 61/148,674, filed on Jan. 30, 2009, provisional application No. 61/148,852, filed on Jan. 30, 2009, provisional application No. 61/110,393, filed on Oct. 31, 2008, provisional application No. 61/110,239, filed on Oct. 31, 2008, provisional application No. 61/110,066, filed on Oct. 31, 2008.

(51) Int. Cl.
*A61N 1/04* (2006.01)

(52) U.S. Cl.
USPC .............................. 607/116; 607/117

(58) Field of Classification Search
USPC .......... 607/2, 5, 9, 39–46, 115–118, 126–131
See application file for complete search history.

(56) References Cited

U.S. PATENT DOCUMENTS

| 3,424,895 A | 1/1969 | Olson |
| 3,649,830 A | 3/1972 | Sato et al. |
| 4,026,301 A | 5/1977 | Friedman et al. |
| 4,374,382 A | 2/1983 | Markowitz |
| 4,628,933 A * | 12/1986 | Michelson ...................... 607/53 |
| 4,727,877 A * | 3/1988 | Kallok ............... 607/5 |
| 4,969,468 A * | 11/1990 | Byers et al. ................... 600/373 |
| 4,987,897 A | 1/1991 | Funke |
| 5,117,824 A | 6/1992 | Keimel et al. |
| 5,261,400 A | 11/1993 | Bardy |
| 5,292,338 A | 3/1994 | Bardy |
| 5,374,287 A * | 12/1994 | Rubin ........................... 607/131 |
| 5,515,848 A * | 5/1996 | Corbett et al. ................ 600/377 |
| 5,545,186 A | 8/1996 | Olson et al. |
| 5,643,330 A | 7/1997 | Holsheimer et al. |

(Continued)

FOREIGN PATENT DOCUMENTS

| EP | 1584351 A1 | 10/2005 |
| WO | WO 98/30280 | 7/1998 |
| WO | WO-2008/073235 A1 | 6/2008 |
| WO | WO 2009/073891 | 6/2009 |

OTHER PUBLICATIONS (PCT/US2010/043361) PCT Notification of Transmittal of the International Search Report and the Written Opinion of the International Searching Authority.

*Primary Examiner* — Allen Porter, Jr.
(74) *Attorney, Agent, or Firm* — Carol F. Barry

(57) ABSTRACT

A medical device includes an implantable device having a processor, a pulse generator and a first lead having first and second ends. The first end of the lead is operably and conductively coupled to the implantable device. A first electrode is operably and conductively coupled to the second end of the first lead. The first electrode has a sharp tip for transmitting and focusing a stimulation signal from the pulse generator to a tissue site.

25 Claims, 9 Drawing Sheets

(56) References Cited

U.S. PATENT DOCUMENTS

| | | | |
|---|---|---|---|
| 5,722,994 A * | 3/1998 | Noren et al. | 607/5 |
| 5,755,736 A | 5/1998 | Gillberg et al. | |
| 5,871,511 A * | 2/1999 | Bolz et al. | 607/14 |
| 5,913,876 A * | 6/1999 | Taylor et al. | 607/2 |
| 6,006,135 A | 12/1999 | Kast et al. | |
| 6,073,048 A | 6/2000 | Kieval et al. | |
| 6,134,470 A | 10/2000 | Hartlaub | |
| 6,208,893 B1 | 3/2001 | Hofmann | |
| 6,745,079 B2 | 6/2004 | King | |
| 6,970,746 B2 * | 11/2005 | Eckmiller et al. | 607/116 |
| 7,010,345 B2 | 3/2006 | Hill et al. | |
| 7,076,283 B2 | 7/2006 | Cho et al. | |
| 7,096,064 B2 | 8/2006 | Deno et al. | |
| 7,218,964 B2 | 5/2007 | Hill et al. | |
| 7,266,414 B2 * | 9/2007 | Cornelius et al. | 607/122 |
| 7,519,428 B1 | 4/2009 | Palmer | |
| 2001/0001126 A1 | 5/2001 | Cammilli et al. | |
| 2002/0107553 A1 | 8/2002 | Hill et al. | |
| 2003/0170898 A1 * | 9/2003 | Gundersen et al. | 435/461 |
| 2004/0249420 A1 * | 12/2004 | Olson et al. | 607/9 |
| 2005/0065570 A1 | 3/2005 | Stein et al. | |
| 2005/0149133 A1 | 7/2005 | Libbus et al. | |
| 2005/0149148 A1 * | 7/2005 | King | 607/70 |
| 2005/0197680 A1 | 9/2005 | DelMain et al. | |
| 2006/0009814 A1 * | 1/2006 | Schulman | 607/45 |
| 2006/0052835 A1 * | 3/2006 | Kim et al. | 607/46 |
| 2006/0095080 A1 | 5/2006 | Libbus et al. | |
| 2006/0241699 A1 | 10/2006 | Libbus et al. | |
| 2007/0073357 A1 | 3/2007 | Rooney et al. | |
| 2007/0150011 A1 | 6/2007 | Meyer et al. | |
| 2007/0156200 A1 | 7/2007 | Kornet et al. | |
| 2007/0239215 A1 | 10/2007 | Bhunia et al. | |
| 2007/0239229 A1 | 10/2007 | Masoud et al. | |
| 2007/0260283 A1 | 11/2007 | Li | |
| 2007/0276443 A1 | 11/2007 | Shafer et al. | |
| 2008/0015659 A1 | 1/2008 | Zhang et al. | |
| 2008/0021507 A1 | 1/2008 | Libbus et al. | |
| 2008/0147140 A1 | 6/2008 | Ternes et al. | |
| 2008/0167696 A1 | 7/2008 | Cates et al. | |
| 2008/0208290 A1 | 8/2008 | Phillips et al. | |
| 2008/0215118 A1 | 9/2008 | Goetz et al. | |
| 2009/0026201 A1 | 1/2009 | Hall et al. | |

* cited by examiner

IMPLANTABLE THERAPEUTIC NERVE STIMULATOR

CROSS-REFERENCE TO RELATED APPLICATIONS

This application claims the benefit of U.S. Provisional Application No. 61/110,300 filed on Oct. 31, 2008.
This application claims the benefit of U.S. Provisional Application No. 61/148,674, filed on Jan. 30, 2009.
This application claims the benefit of U.S. Provisional Application No. 61/148,852, filed on Jan. 30, 2009.
This application claims the benefit of U.S. Provisional Application No. 61/110,393, filed on Oct. 31, 2008.
This application claims the benefit of U.S. Provisional Application No. 61/110,239, filed on Oct. 31, 2008.
This application claims the benefit of U.S. Provisional Application No. 61/110,066, filed on Oct. 31, 2008.
This application is related to U.S. patent application Ser. Nos. 12/362,814; 12/362,822; 12/362,773, now U.S. Pat. No. 8,005,539; Ser. Nos. 12/362,809; 12/362,781; 12/362,838; 12/362,842; 12/362,768; 12/362,859; 12/362,662; 12/363,375; 12/363,215; 12/363,180 all of which were filed on Jan. 30, 2009.
The disclosures of the above applications are incorporated herein by reference.

INTRODUCTION

Various implantable devices include pulse generators for providing therapy by stimulating tissue.
The present teachings are directed to an implantable device for providing therapy using novel features that may enhance the efficacy of stimulation delivery.

SUMMARY

In various embodiments, the present teachings provide a medical device that includes an implantable device having a processor, a pulse generator and a first lead having first and second ends. The first end of the lead is operably and conductively coupled to the implantable device. A first electrode is operably and conductively coupled to the second end of the first lead. The first electrode has a sharp tip for transmitting and focusing a stimulation signal from the pulse generator to a tissue site.
In various embodiments, the present teachings provide a medical device that includes an implantable device including a pulse generator. The medical device includes a plurality of electrodes operably and conductively coupled to the implantable device. At least a first electrode of the plurality electrodes having a sharp tip for transmitting and focusing a stimulation signal from the pulse generator to a tissue site.
In various embodiments, the present teachings provide a method of delivering tissue stimulation including generating an electrical stimulation signal from a signal generator of an implantable medical device, positioning a first sharp tip of a first electrode in contact with tissue, wherein the first electrode is conductively and operably coupled to the implantable medical device, and transmitting the signal to the tissue through the first sharp tip.
Further areas of applicability of the present teachings will become apparent from the description provided hereinafter. It should be understood that the description and specific examples are intended for purposes of illustration only and are not intended to limit the scope of the present teachings.

BRIEF DESCRIPTION OF THE DRAWINGS

The present teachings will become more fully understood from the detailed description and the accompanying drawings, wherein.

DESCRIPTION OF VARIOUS ASPECTS

The following description is merely exemplary in nature and is in no way intended to limit the present teachings, applications, or uses.
The present teachings provide an implantable nerve stimulator that can be used with peripheral nerve stimulation, spinal cord stimulation or other neurostimulation for various therapeutic outcomes including, but not limited to, changes in autonomic nervous system function, cardiac and cardiovascular therapy. For example, the present teachings can be used in therapies for electromechanical dissociation (EMD), to improve rapid cardiac recovery after defibrillation, to facilitate rapid restoration of normal sinus rhythm, to enhance blood pressure conditions, and provide cardioprotective and cardiovascular benefits. Cardioprotective benefits may include reduction or elimination of one or more of conditions including fibrillation or tendency toward fibrillation, tachycardia, unhealthy cardiac contractions, ischemia, inefficient heart pumping, inefficient collateral circulation of heart, cardiac muscle trauma, defibrillation energy, and other cardiac conditions. Additionally, the present teachings can be used for providing blocking stimulation, as discussed below.

Figure 1:
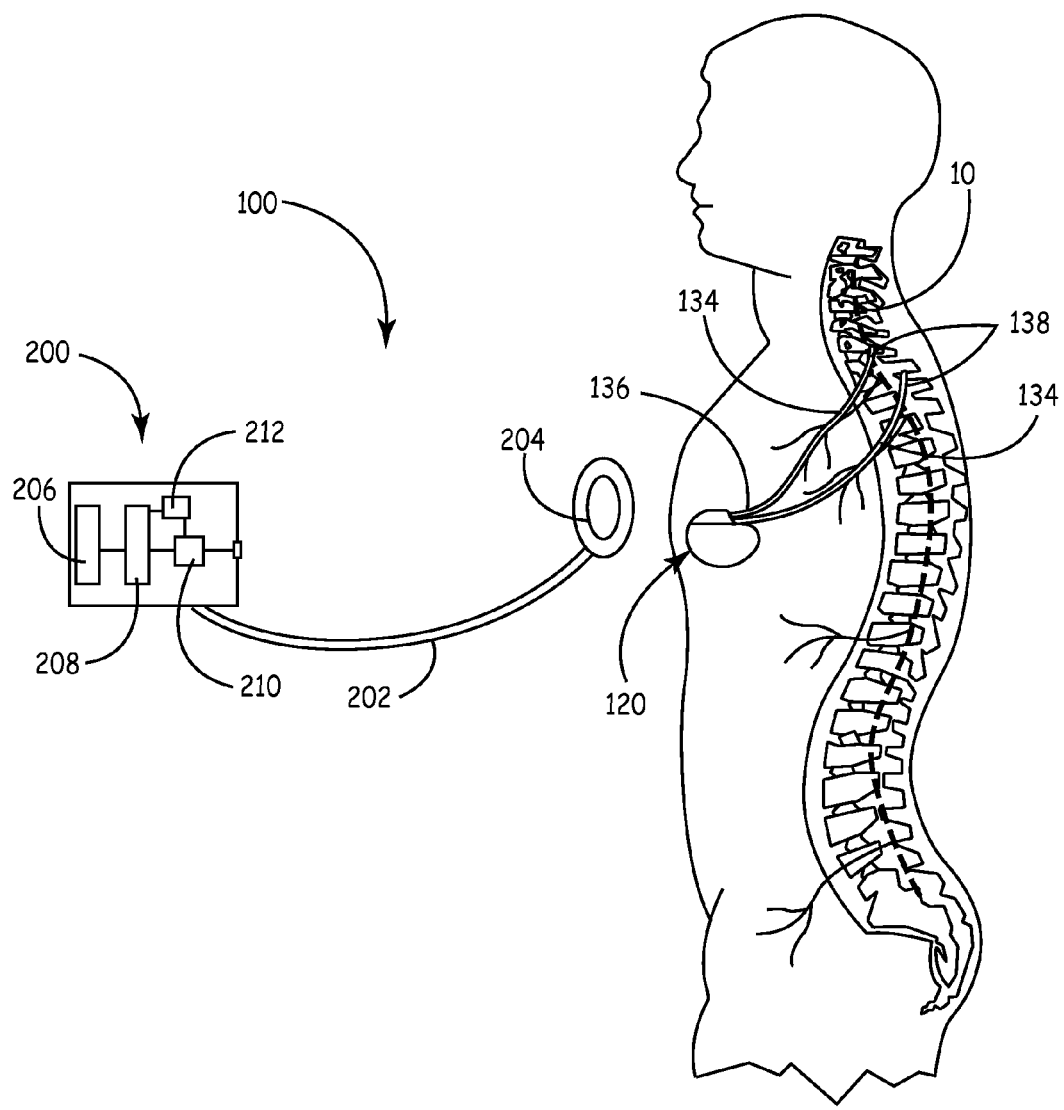
FIG. 1 is an environmental illustration of an implantable nerve stimulator according to the present teachings.
Figure 6A:
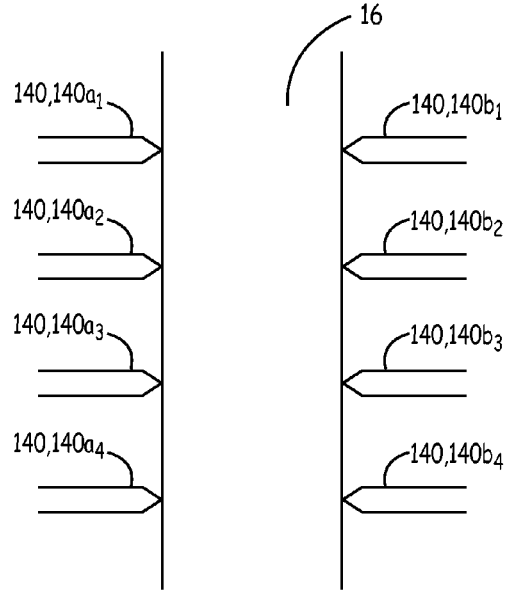
FIG. 6A is an environmental side view of a plurality of electrodes of an implantable nerve stimulator according to the present teachings.
Figure 6C:
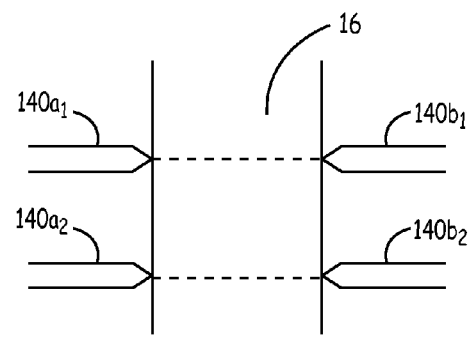
FIG. 6C is an environmental side view of first and second pairs of electrodes of an implantable nerve stimulator according to the present teachings.
Figure 6D:
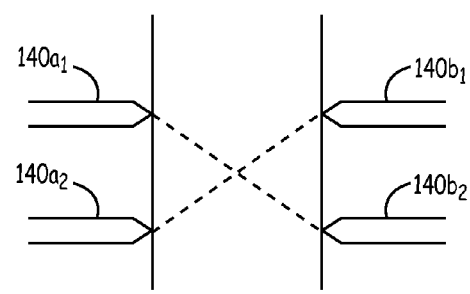
FIG. 6D is an environmental side view of first and second pairs of electrodes of an implantable nerve stimulator according to the present teachings.
Figure 6B:
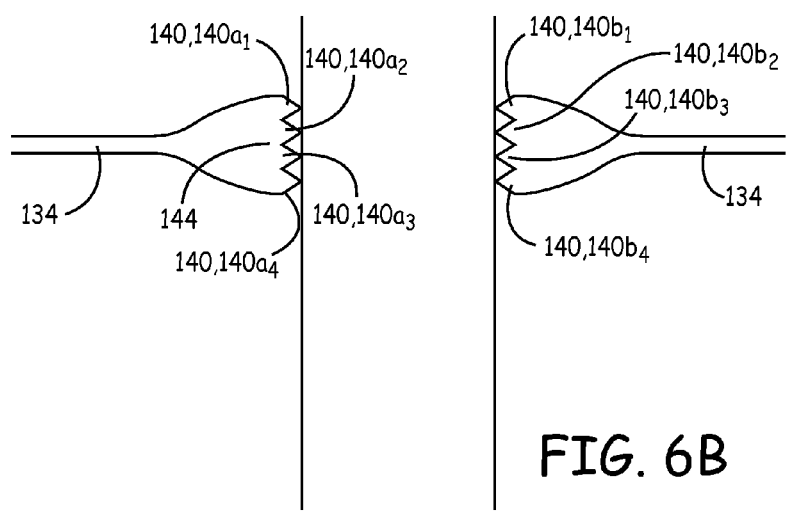
FIG. 6B is an environmental side view of a plurality of electrodes of an implantable nerve stimulator according to the present teachings.
Figure 7:
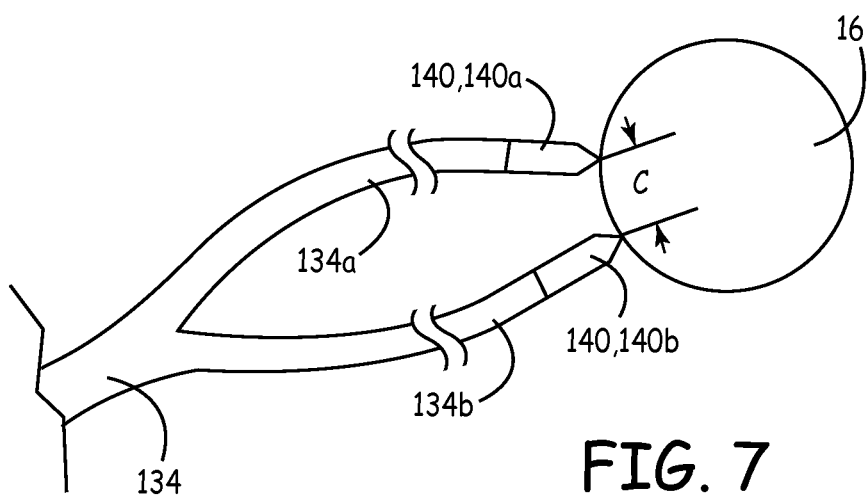
FIG. 7 is a sectional environmental view of a pair of electrodes of an implantable nerve stimulator according to the present teachings.

An exemplary nerve stimulation apparatus 100 according to the present teachings is illustrated schematically in an environmental view in FIG. 1. The nerve stimulation apparatus 100 can include an implantable device 120 which can be implanted subcutaneously in a patient. The nerve stimulation apparatus 100 can include one or more leads 134 for delivering nerve stimulation and or sensing. The lead 134 can incorporate unipolar or bipolar stimulation electrode arrangements. The lead 134 can also include sensing electrodes. The lead 134 and electrode arrangements can be, for example, in the form of various leads and electrode arrangements, such as those as disclosed in commonly owned U.S. Pat. No. 6,073,048 issued Jun. 6, 2000, in commonly owned U.S. Pat. No. 6,745,079 issued Jun. 1, 2004, or in commonly owned U.S. Patent Publication 2007/0073357, published on Mar. 29, 2007, and in commonly owned and currently pending patent application Ser. No. 12/363,215, filed on Jan. 30, 2009 and Ser. No. 12/362,859 filed on Jan. 30, 2009, the disclosures of each of which are incorporated herein by reference. For bipolar electrode applications corresponding pairs of electrodes can be coupled to separate leads 134, as shown, for example, in FIGS. 1-3 or separate lead arms 134a, 134b of a bifurcated lead 134, as shown in FIG. 7. It will be appreciated that bifurcated leads with two lead arms can be used interchangeably with a pair of separate leads in the various embodiments described herein. The electrodes of the lead 134 are referenced with numeral 140 and described in connection with FIGS. 5A-7 below.

Figure 2:
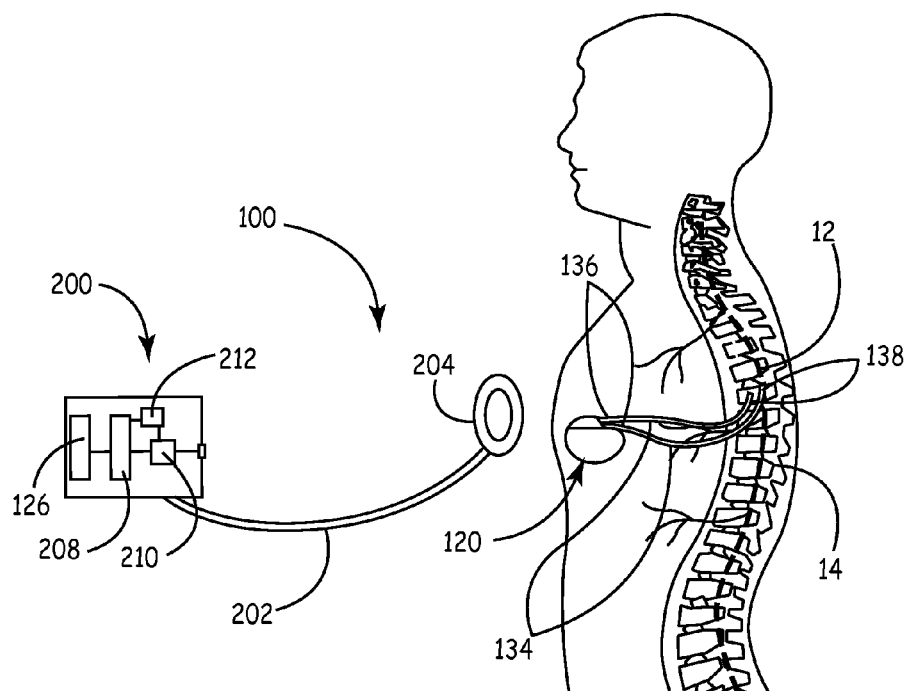
FIG. 2 is an environmental illustration of an implantable nerve stimulator according to the present teachings.
Figure 3:
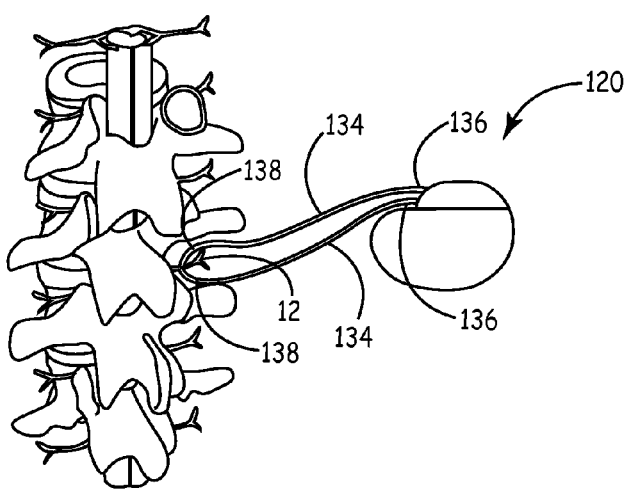
FIG. 3 is an environmental illustration of an implantable nerve stimulator according to the present teachings.
Figure 4:
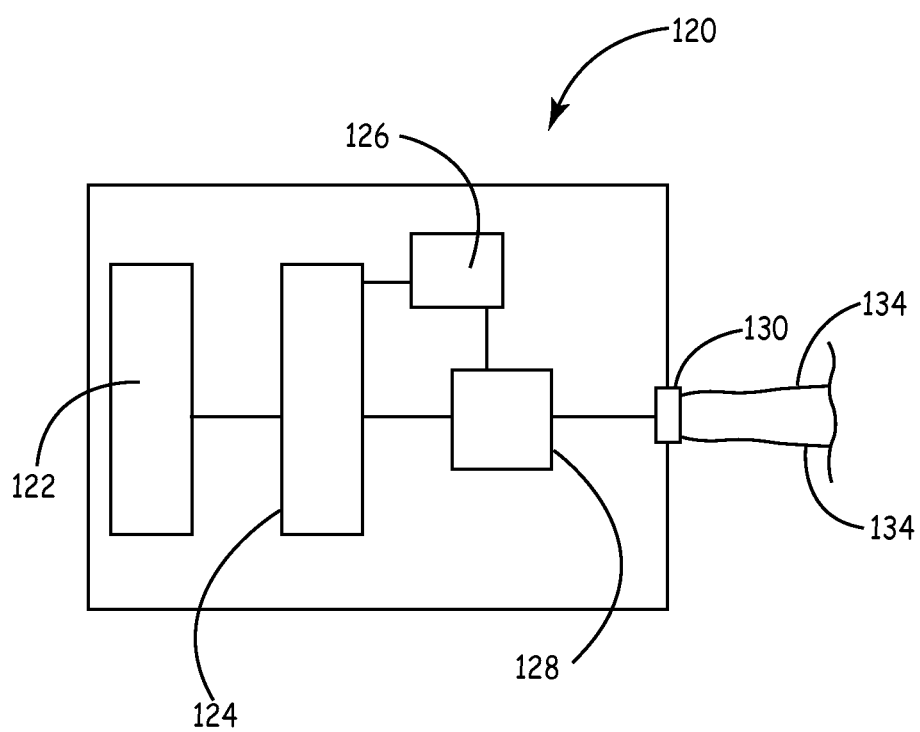
FIG. 4 is a schematic illustration of an implantable nerve stimulator according to the present teachings.

The lead (or lead arms or leads) 134 can be operably coupled to the implantable device 120 at a connector 130, as shown in FIG. 4. The lead 134 can have a first end 136 coupled to the implantable device 120 and a second end 138 positioned adjacent or in contact to a tissue site selected for therapeutic stimulation. The tissue site can be a vagus or neck nerve 10, as illustrated in FIG. 1, or a spinal nerve 14 that extends from the sympathetic trunk 12 along the spine of the patient, as illustrated in FIGS. 2 and 3. In one aspect, the electrodes of the lead 134 can be placed in contact with a nerve root extending from the epidural space. In another aspect, the electrodes of the lead 134 can be placed between the nerve branch exiting between adjacent thoracic vertebrae, such as vertebrae T5 and T6, for example.

The nerve stimulation apparatus 100 can also include an external programmer/controller 200 that can communicate wirelessly with the implantable device 120, as illustrated in FIG. 1. The programmer 200 can include, for example, a conductor 202 coupled to a radio-frequency antenna 204 for radio-frequency communication with the implantable device 120 after implantation.

The programmer 200 can be, for example, a wireless telemetry programmer, such as one of the models of the Medtronic CareLink® programmers, which are commercially available from Medtronic, Inc., Minneapolis, Minn. This Medtronic CareLink® programmer uses the Medical Implant Communications (MICS) radio frequency band and is configured to automatically search for the clearest MICS channel available. The programmer 200 can include a power supply 206, data storage 208 and processor circuitry 210 including receiver, transmitter, storage and wireless communication modules, and optionally an internet module 212 with Wi-Fi, 3G or other internet communication capability. The programmer 200 can be operable to interrogate the implantable device 120, receive data from the implantable device 120, and transmit data to the implantable device 120 and generally program the implantable device 120. The programmer 200 can also be in the form of an internet-based handheld wireless monitor, such as the CareLink® Monitor, commercially available from Medtronic, Inc., Minneapolis, Minn., can be included as part of the nerve stimulation apparatus 100 and can be used by the patient to send data to a clinic or physician's office via a standard phone line.

Referring to FIG. 4, the implantable device 120 can include a power supply 122, a processor 124, and a communications module 126. The implantable device 120 can also include a neurological/stimulation signal or pulse generator 128 coupled to the connector 130. The pulse generator 128 can be integral with the implantable device 120, as illustrated in FIG. 3, or a separate implantable device, such as, for example, the pulse generator Itrel II® or Synergy®, which are commercially available from Medtronic, Inc., Minneapolis, Minn.

The processor 124 can be programmed to instruct the communications module 126 to communicate wirelessly with a medical alert system or with a patient's wireless communication device, including a cell phone or a medical monitor or programmer 200 for transmitting information automatically to a medical center. The processor 124 can be programmed to instruct the pulse generator 128 to provide nerve stimulation via the lead 134 according to a predetermined or updated or revised schedule. The stimulation delivery aspects provided by the processor 124 and the pulse generator can operate, for example, as described in commonly owned U.S. Pat. No. 6,073,048, U.S. Pat. No. 6,745,079, and U.S. Patent Publication 2007/0073357, referenced above. For example, the processor 124 can transmit an electrical stimulation signal via the lead 134 to stimulate or reduce parasympathetic or sympathetic nerve activity, as appropriate for a particular patient. The process can be repeated until selected and/or monitored physiological conditions of the patient return to normal or to a predetermined level. The processor 124 can also include crosstalk mitigation modules or functions to prevent natural induced signals or signals from other implantable devices or electrodes from passing temporarily through the nerve during the brief duration of active nerve stimulation therapy, as described, for example, in commonly assigned and currently pending U.S. application Ser. No. 12/363,180, filed on Jan. 30, 2009 and incorporated herein by reference.

The lead 134 can be implanted by local incision near a selected implantation site for providing nerve stimulation and/or sensing nerve activity. The implantable device 120 can be inserted subcutaneously using a tunneling tool in a desired location in proximity to and for coupling with the lead 134. Various tunneling tools are commercially available from Medtronic, Inc., Minneapolis, Minn.

The implantable device 120 can be combined with additional therapy or monitoring modules, such as modules for blood pressure therapy, pacemaker therapy or other cardiac synchronization therapies either incorporated within the implantable device 120 or provided by separate implantable devices, as described, for example, in commonly assigned and co-pending patent application Ser. No. 12/363,215 filed on Jan. 30, 2009, the disclosure of which is incorporated herein by reference.

Figure 5A:
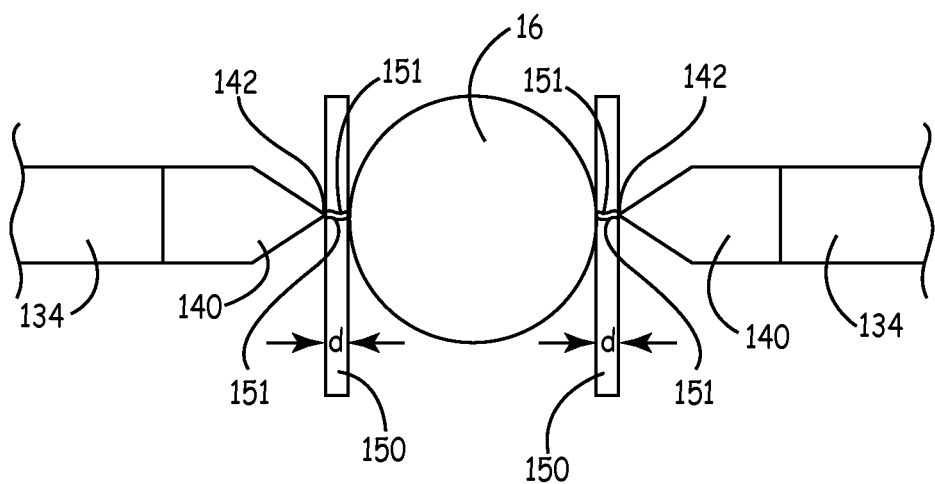
FIG. 5A is a sectional environmental view of a pair of electrodes of an implantable nerve stimulator according to the present teachings.
Figure 5B:
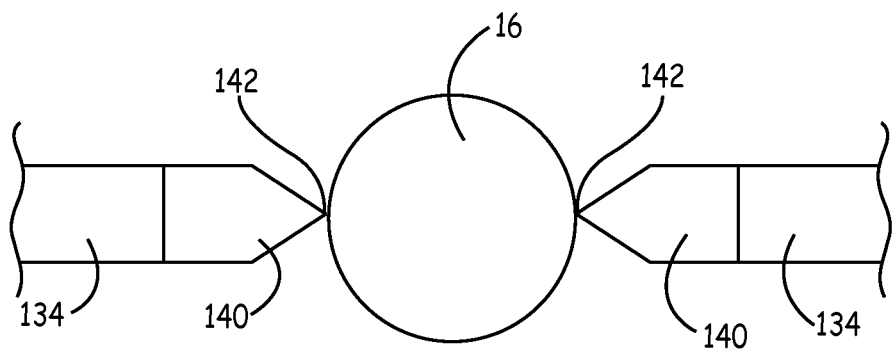
FIG. 5B is a sectional environmental view of a pair of electrodes of an implantable nerve stimulator according to the present teachings.

Referring to FIG. 5A, nerve stimulation can be provided through stimulation signals transmitted to a nerve (or nerve bundle or other tissue) 16 through needle-like, pointed stimulation electrodes 140. Each electrode 140 can be operably and conductively connected to the lead 134 (or to corresponding separate arms 134a, 134b of the same lead 134) and can include a sharp and point-like electrode tip 142 for focused energy/signal transmission. Referring to FIGS. 5A and 5B, two stimulation electrodes 140 positioned at opposite sides of the nerve 16 are illustrated. The sharp tip 142 of the electrode 140 can directly contact the nerve 16, as illustrated in FIG. 5B, or indirectly, through an intermediate nonconductive barrier 150, as illustrated in FIG. 5A. The barrier 150 can be, for example, a film of low dielectric material, or generally a very thin barrier providing mechanical protection to the tissue. The barrier 150 can have a thickness "d" such that the electrically insulative properties of the barrier 150 do not appreciably impede passage of the energy of the stimulation signal through the barrier 150. The thickness d for example can be in the range of about $1 \times 10^{-4}$ of inch to about $3 \times 10^{-3}$ of inch. The barrier 150 can protect tissue from mechanical piercing/stressing or other mechanical damage, while allowing energy discharge through the electrode tip 142 to pass through the barrier 150 into the nerve 16.

The pointed stimulation electrodes 140 can facilitate more efficient voltage discharge through the electrode tips 142 toward and into the nerve 16. First and second plurality of opposing pointed electrodes 142 can be used, for example, as illustrated in FIG. 6A. The pointed stimulation electrodes 142 in the same side of the nerve 16 can also be combined in a one-piece (integral or monolithic) comb-like structure 144, as illustrated in FIG. 6B.

More generally, the pointed stimulation electrodes 140 can be arranged on diametrically opposite sides of the nerve, as illustrated in FIGS. 5A, 5B, 6A and 6B, or alternatively on the same side of the nerve 16, at a circumferential distance "c" which is less than 180 degrees, as illustrated in FIG. 7.

Figure 8:
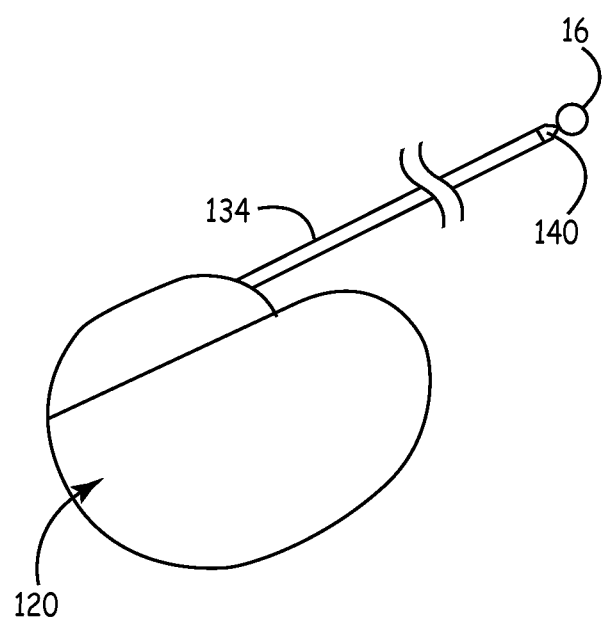
FIG. 8 is an environmental view of a pair of electrodes of an implantable nerve stimulator according to the present teachings.

In other embodiments, only one electrode of a pair of stimulation electrodes 140 (i.e., the pairs shown in FIGS. 5A, 5B, and 6A, for example) may be pointed, while the other electrode need not be pointed. Alternatively, a single pointed electrode 140 can be used with unipolar leads, as shown in FIG. 8, for example, in which the other electrode can be the can or housing of the implantable device 120.

Various types of stimulation can be provided in connection with the nerve stimulation device 100. For example, high-voltage very brief-duration (HVBD) pulses can be used, such as, for example, in the range of about 1 kV to about 10 kV pulse, with pulse duration, for example, of about 10 ns to about 1000 ns. Such a high-voltage very brief-duration pulse can be used as a signal for spinal cord stimulation or other nerve or tissue stimulation. A voltage or current profile similar to an ESD shock delivered by an ESD test machine, such as the Keytek Minizap ESD Simulator, commercially available from MetricTest, Hayward, Calif. 94545 or other distributors, can be used. Generally, the signal provided by any ESD simulator complying with industry standards MIL-STD-883G, or IEC 801-2 or IEC 601-1 can be used to provide a high-voltage very brief-duration pulse through the pointed stimulation electrodes 140. It will be appreciated that although initial voltage delivery is very high, it can quickly drop, as discussed below.

Using a very brief duration pulse of type described above (HVBD) can avoid irreversible damage to the nerves and tissue. Such high-voltage very brief-duration stimulation can create reversible electroporation, and at the same time provide various modes of therapy. For example, the brief pulse can provide stimulation to all the nerves in the vicinity of the stimulation site, or alternatively address particular nerve fibers of the neck or the spinal cord; resulting in cardiac benefits, pain relief or other therapeutic benefits. The pulse rate can be slow or fast, as recommended by a health care professional or as appropriate for the patient and desired therapy. In some therapies, one pulse every 10 minutes and up to once every 1 ms can be used. The brief duration of the generated pulse can reduce cross-talk artifact effects between the stimulation signal from the pulse generator 128 and other implantable cardiac devices, such as an implantable cardioverter/defibrillator device (ICD), which may be either separate or integrated as an additional module into the implantable device 120. A slower stimulator pulse rate can be used with the brief pulse, thereby reducing cross-talk artifact adverse effects into the ICD. Additional aspects of crosstalk mitigation are disclosed in currently pending and commonly assigned patent application Ser. No. 12/362,859, filed on Jan. 30, 2009, and Ser. No. 12/363,215 filed on Jan. 30, 2009, the disclosures of which are incorporated herein by reference. Further, the brief duration and the reduced pulse rate of the stimulation signal tend to reduce the amount of power needed to accomplish the stimulation and obtain cardiac benefits, as compared to a more traditional spinal cord and other nerve stimulation signals.

This high-voltage very brief-duration pulse (HVBD) can be produced in various ways, any of which can be incorporated in the pulse generator 128 for producing a stimulation signal transmitted through the pointed stimulation electrodes 140. In one illustrative example, the HVBD pulse can be produced by generating a high voltage that is stored in a 150 pF capacitor, which is discharged through a 330 ohm resistor into the sharp tips 142 of the stimulation electrodes 140 that are placed across or near or against the tissue or nerve or nerve bundle. The high voltage very brief-duration pulse can also be produced, for example, by using a piezo generator. A piezo generator can include a piezoelectric crystal and a spring-loaded hammer or other component which can be activated to hit and/or otherwise deform the piezoelectric crystal. The sudden forceful deformation of the piezoelectric crystal can produce a high voltage charge, which can be collected via electrodes or other conducting elements coupled to the piezo generator and delivered to the stimulation electrodes 140. The piezo generator can be similar to the piezoelectric igniter on a cigarette or grill lighter, which generates a spark or spark-like high voltage. When the spark or discharge is initiated, conduction is engaged rapidly and the voltage drops quickly between the electrodes 140, because of the voltage drop in the conductive delivery wires and of the rapid discharge of the capacitor. The spark-like discharge can temporarily puncture a hole or widen a pore in the nerve cell membrane in the form of electroporation, which causes the nerve to be stimulated or to emit neuro-chemicals/hormones or causes the nerve to temporarily be blocked from relaying electrical signals robustly.

The barrier 150 can be in the form of an insulative layer, having a breakdown or pass-through voltage in the range of about 50V to about 1 KV, for example. The spark-like voltage can pass through the insulative barrier 150, because of a temporary breakdown or breach in the insulation properties of the barrier 150. The insulative barrier 150 can also help enable the rapid rise time delivery of the spark. Since the voltage can be ramped up by a circuit, as the voltage rises, the breakdown of the insulative barrier 150 can cause an avalanche breakdown and a rapid discharge into the tissue. The barrier 150 can be made of silicone or other materials, including porous insulative materials or composites.

In other embodiments, the barrier 150 can be in the form of an insulative layer that includes one or more pores or micro pores or micro holes or other small openings, defining corresponding one or more passages 151 through the width d of the barrier. The passages 151 can range in diameter size from about $1 \times 10^{-6}$ of an inch to about $1 \times 10^{-3}$ of an inch, for example. The passages 151 can be straight, such as perforations made laser, or can be tortuous or meandering passages, such as passages in fiber-like materials. At least some passages 151 can be in the vicinity of the sharp tip 142 of the corresponding electrode 140, when the electrode 140 is placed in contact with the barrier 150. As the high voltage is focused by the electrodes 140, the passages 151 can facilitate the passing of the voltage through the passages 151, such that the breakdown or pass-through voltage for the barrier 150 can be lower than it would be for a non porous barrier or a barrier without such passages 151. Therefore, for a barrier 150 having pores or passages 151, the breakdown voltage can be a much lower voltage, such as in the hundreds of volts, for example, since energy can pass through the pores and does not have to pass through a contiguous or nonporous solid insulative layer.

Another illustrative example for producing a HVBD pulse includes harnessing the high voltage of the flyback effect produced when a coil is pulsed. The spark-like high voltage can be conducted to the stimulation electrodes 140 and provide therapeutic stimulation.

In yet another example, a large turns ratio transformer of the type used in older automobile ignition coils can be used to produce the high voltage that is applied to the stimulation electrodes 140.

Additionally, instead of a DC high voltage pulse, a biphasic high voltage pulse can be used, or the signal can alternate between positive and negative pulses or strings of high voltage pulses or low voltage pulses. Alternatively, white noise, pink noise, narrow band noise, or pseudo-noise can be used as the signal pattern in a low voltage or a high voltage output. The noise pattern can be applied in brief durations, such as lasting 10-450 ns, with a repetition rate of 1-100 Hz. In other embodiments, the noise signal can be constant or of a brief duration lasting from one to several milliseconds. The noise stimulation signal can also be used with non-pointed electrodes.

Figure 9A:
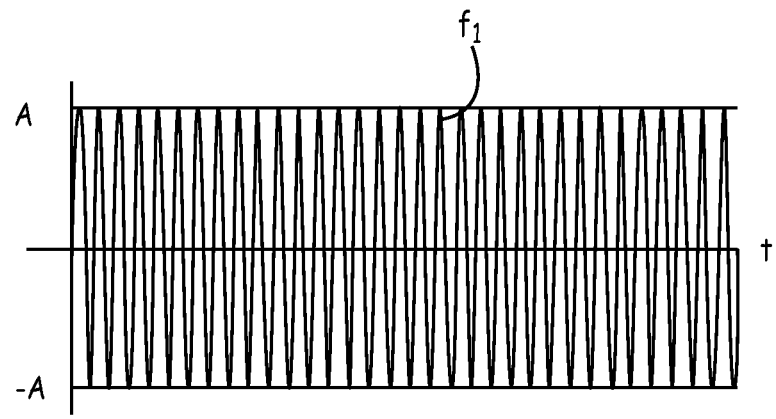
FIG. 9A is a diagram of an exemplary stimulation signal at a first frequency for an implantable nerve stimulator according to the present teachings.
Figure 9B:
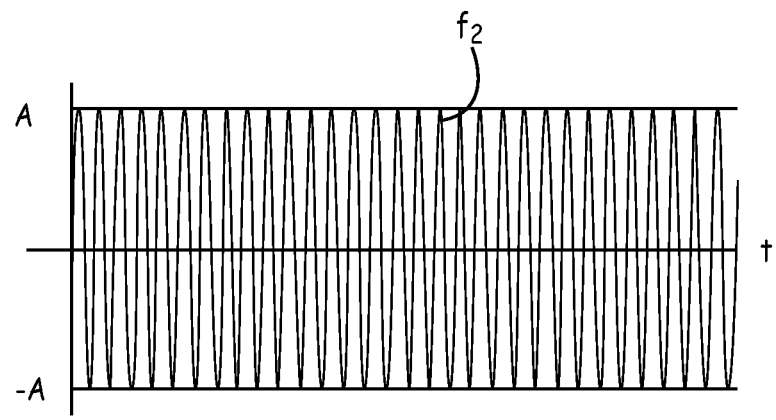
FIG. 9B is diagram of an exemplary stimulation signal at a second frequency for an implantable nerve stimulator according to the present teachings.
Figure 9C:
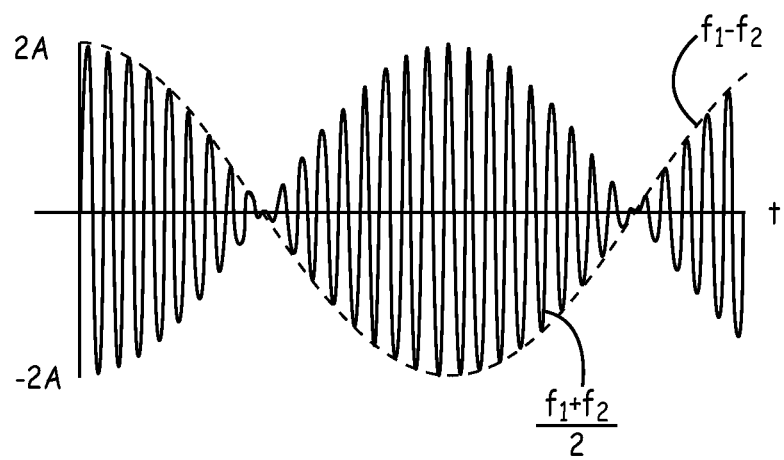
FIG. 9C is diagram of an exemplary pulse signal resulting from the interaction of the stimulation signals of FIGS. 9A and 9B for an implantable nerve stimulator according to the present teachings.

In another aspect, the stimulation electrodes 140 can be used to transmit interferential stimulation pulses. First and second pairs of stimulation electrodes E ($140a_1$, $140b_1$) and D ($140a_2$, $140b_2$) can be arranged in various patterns, such as a square pattern illustrated in FIG. 6C or a cross connection pattern illustrated in FIG. 6D. The individual electrodes $140a_1$, $140b_1$, $140a_2$, $140b_2$ can be also positioned in an interleaved or a sequentially staggered arrangement (not shown). The first pair of stimulation electrodes E can be driven with a first signal of a first frequency $f_1$, as shown in FIG. 9A, and the second pair of electrodes D can be driven with a second signal of a different second frequency $f_2$, as shown in FIG. 9B. The first and second signals can intersect across the tissue or nerve 16 and produce a stimulation signal that may not be achievable with only one source of stimulation energy, as illustrated in FIG. 9C. In an exemplary embodiment, the first frequency $f_1$ can be very close in magnitude to the second frequency $f_2$, such as, for example $f_1$=100 Hz and $f_2$=101 Hz. Alternatively, the first frequency $f_1$ can be far from the second frequency $f_2$, such as $f_1$=100 Hz and $f_2$=10 kHz.

The first and second frequencies $f_1$ and $f_2$ can be very high frequencies, such as in the range of about 10 to 100 kHz, and the beating of the first frequency $f_1$ against the second frequency $f_2$ can produce a form of tissue-based demodulation that serves as nerve stimulation. For example, the combination of $f_1$=20 kHz and $f_2$=20.1 kHz can result in non-linear demodulation by the tissue and a resultant stimulation at ($f_1-f_2$)=100 Hz or other frequencies. The first and second frequencies $f_1$ and $f_2$ can be selected to result in targeted stimulation of particular fibers or fiber types. Fluctuating frequencies can also be used, such that the signal can sweep through a range of frequencies resulting from sums/differences to obtain various stimulation benefits and various stimulations customized for specific nerve fiber type stimulation and specific nerve fiber locations, including the vagus nerve, spinal cord nerves or other nerve fibers.

Figure 10A:
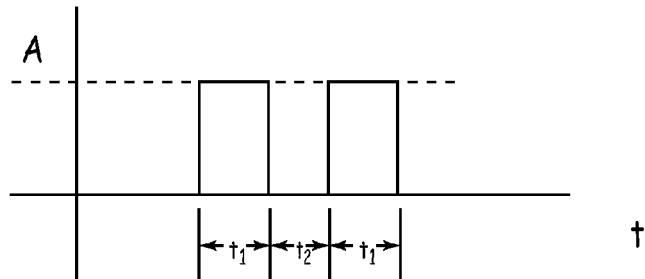
FIG. 10A is an amplitude versus duration diagram of a representative stimulation signal for an implantable nerve stimulator according to the present teachings.

Various stimulation sequences and treatment protocols or schedules can be programmed in the processor 124 and used for stimulation of various tissues or nerves, including the vagus nerve and the spinal cord nerves. For example, spinal cord stimulation can be used for cardiac benefits and other benefits, using a stimulation signal that is not continuously applied at the highest energy target level. In a first exemplary treatment protocol illustrated schematically in FIG. 10A, the spinal cord stimulation is applied on and off at the highest/target stimulation/energy level A. Accordingly, the stimulation signal is applied for a time duration $t_1$, which can be a few seconds, a few minutes, a few hours or a few days depending on the treatment. The stimulation is then turned off (or applied at a reduced energy level) for a time duration $t_1$, which can be a few hours or a few days, and then the cycle repeats over and over again.

Figure 10B:
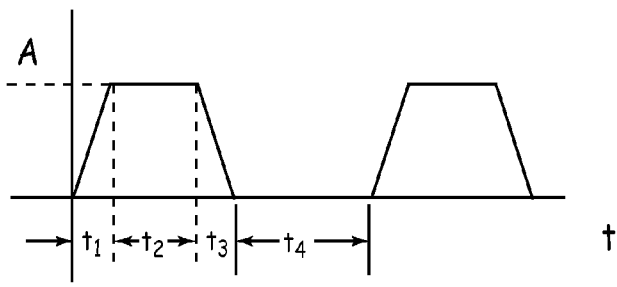
FIG. 10B is an amplitude versus duration diagram of a representative stimulation signal for an implantable nerve stimulator according to the present teachings.

In a second exemplary treatment protocol illustrated schematically in FIG. 10B, the spinal cord stimulation can be turned on and ramped gradually to a target stimulation/energy level A (level for full therapy) at a time duration $t_1$. The signal can be kept at the target level A for a time duration $t_2$ and then ramped down to off over a time duration interval $t_3$. The time durations can be determined for reaching a target level of effectiveness or treatment. Then the spinal cord stimulation can be turned off (or applied at a reduced energy level) for a time duration $t_4$, which could be a few hours or a day or a few days. Subsequently, the spinal cord stimulation can be turned on again (or resume at higher energy level), and the cycle can be repeated.

Figure 10C:
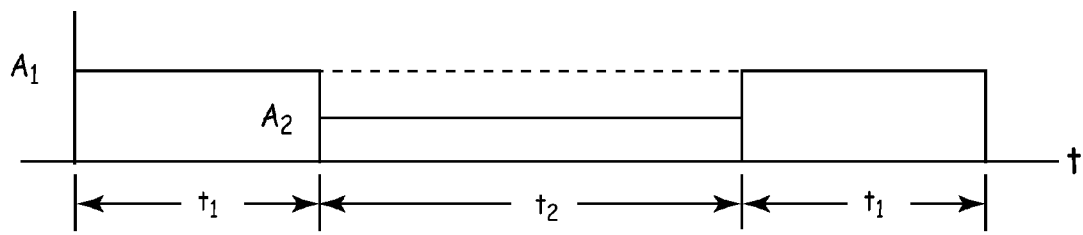
FIG. 10C is an amplitude versus duration diagram of a representative stimulation signal for an implantable nerve stimulator according to the present teachings.

In a third exemplary treatment protocol illustrated schematically in FIG. 10C, spinal cord stimulation for cardiac or other therapy is provided using a stimulation signal that is not continuously applied at initial target/therapy levels. For example, spinal cord stimulation can be applied at full therapy stimulation level $A_1$, which can include the largest intended voltage, the longest intended duration, the most electrodes, the most power utilized from the battery, etc. Stimulation at this therapy stimulation level can be remain in effect for a time duration $t_1$, until a desired amount of therapy is applied at this level of stimulation, such as for a few days, a week, etc; or until a feedback mechanism, such as a sensor providing corresponding activity (heart rate, blood pressure, etc.) indicates that sufficient amount of therapy has been applied. Then spinal cord stimulation can be applied at reduced therapy stimulation level $A_2$, i.e., less than largest intended voltage, less than longest intended duration, fewer electrodes, etc; and thus less power utilized from the battery. The stimulation can remain in effect indefinitely at the reduced level $A_2$. Alternatively, after a time duration $t_2$, such as once a day or once a week, stimulation can be returned to level $A_1$ for a time duration equal or less than $t_1$, after which stimulation at reduced level $A_2$ can be resumed and the cycle can be repeated periodically.

The protocols discussed above in connection with FIGS. 10A, 10B and 10C are based on the ability of spinal cord stimulation (SCS) first to provide therapeutic benefits that continue subsequent to halting SCS; and second to initially require a larger stimulation level, which can later be reduced to smaller stimulation level, yet remain therapeutically effective at the reduced stimulation level. Some of these results were observed by the Applicant in a limited experimental setting conducted in preparation for the present disclosure and using known, not pointed electrodes. In particular, after SCS was applied to reduce heart rate in a canine subject, the resulting beneficial low heart rate was sustained for a duration of several minutes after SCS was discontinued. Further, the sustained duration of low heart rate was more prolonged with long pulse durations of 120-450 μs, and less prolonged with shorter pulse durations of 60 μs. The experimental results appear to validate that spinal cord stimulation exhibits a lingering effect which allows spinal cord stimulation to be applied intermittently, and yet obtain the desired benefits. In some procedures, the "on" time of the stimulation signal can be very brief, such as in the range of about 0.1 second to about 1 second. The "off" time of the stimulation signal can also be brief such as in the range of about 0.1 second to about 20 seconds.

Potential mechanisms that may contribute to the ability to intermittently stimulate with SCS yet obtain on-going benefits include the potential creation of neurochemicals by the body via SCS stimulation, which have ongoing presence after SCS is "off". Thus, the neurochemicals may provide the therapeutic benefits that continue for a period of time, such as seconds, minutes, hours, or days, after SCS signal is switched off, as discussed above. Alternatively or additionally, the nerves being stimulated by SCS may be placed into a semi-habitual self-stimulating or excitation mode due to the SCS. Thus, these nerves continue to fire after SCS is turned "off". The self-stimulating nerve firing can provide on-going benefits that continue for a period of time, such as seconds, minutes, hours, or days, as discussed above.

The use of intermittent SCS also helps reduce the amount and impact of cross-talk artifact of SCS signals fed into other devices such as ICD; enabling the concurrent use of an SCS device with other devices. These results can also be applied to vagal stimulation.

Additionally, spinal cord stimulation for cardiac benefits and other benefits can be applied using a stimulation signal that is sequentially applied to different pairs electrodes, such as the eight electrode array with four pairs of electrodes 140 (140$a_1$ and 140$b_1$; 140$a_2$ and 140$b_2$; 140$a_3$ and 140$b_3$; 140$a_4$ and 140$b_4$) shown in FIG. 6A. Stimulation through selected pairs of electrodes 140 can be applied sequentially in time but with different pairs of electrodes selected at a time for various possible combinations. For example, a stimulation signal can be applied between the pair 140$a_1$ and 140$b_1$ for 5-60 minutes, followed by a stimulation signal applied between the pair 140$a_3$ and 140$b_3$ for 5-60 minutes. Other combinations can also be used, including interleaved or cross combinations as shown in FIG. 6D. For example, a stimulation signal can be applied between the pair 140$a_1$ and 140$b_2$ for 5-60 minutes, followed by a stimulation signal applied between the pair 140$a_2$ and 140$b_3$ for 5-60 minutes, etc. The actual electrodes selected and the actual time that stimulation signal is applied can vary.

The sequence and duration and selection of electrodes/location for stimulation can be determined for reducing or preventing erosion of therapy efficacy. Additionally, the sequential stimulation can reduce the amount of time that a particular tissue site is stimulated. Accordingly, the stimulation protocols and schedules described above can help reduce the amount of energy needed to obtain and maintain therapy, thereby helping to keep the tissue responsive to stimulation by reducing the amount of continuous stimulation to a given location. Additionally, the stimulation protocols discussed above can reduce the time that the patient might feel the stimulation.

In exemplary embodiments, the spinal cord stimulation signal can be a signal with 10 Hz to 100 Hz pulse rate, with duration of 50-500 μs, and with a voltage of about 1V to about 12 V. This low voltage stimulation can be used without the barriers 150, such that the low voltage is not overcome by the barriers 150. In other embodiment, however, a localized electric field can be set up upon the nerve, even with the presence of a barrier 150 and even with relatively low voltage. Other stimulation signals can be used, such as the other ones described above or in the cross-referenced patent applications.

The stimulation signals of the present teachings can also induce a temporary nerve block that prevents or attenuates natural induced signals or signals from other implantable devices and electrodes from passing temporarily through the nerve during the brief duration of active nerve stimulation therapy. This block effect can be present in both the spark-like nerve stimulation and in the electric field nerve stimulation described herein. Further, a synchronization schedule can be implemented to optimize separate therapy functions provided by different electrodes or different implantable devices associated with different therapies in the same patient. For example, vagus stimulation can be scheduled to avoid instantaneous overlap with spinal chord stimulation, although the corresponding stimulation signals can be interlaced in time. Similarly, pacing or other cardioverter activity can be scheduled to avoid instantaneous overlap with nerve stimulation activity, although the corresponding stimulation signals can be interlaced in time. By synchronizing the various therapy schedules, multiple signals associated with different therapies can be activated serially in an interpolating/interlacing manner, similar to the operation of serial computing. In other words, a single pulse of first therapy signal that includes a sequence of pulses can be transmitted during a non-active or off period of a second therapy signal, and conversely, thereby optimizing the efficiency of multiple therapies. The synchronization can be implemented in the processor 124 or built in into the signal schedules of each separate therapy mode.

In another embodiment, undesirable stimulation of other non-targeted body regions during stimulation of a targeted nerve can be blocked by transmitting simultaneously therapy and blocking signals in different directions. For example, when a first or therapy stimulation signal is transmitted through a first set (or therapy set) of electrodes 140 to a vagus nerve 10 for therapeutic purposes, as shown for example in FIG. 2, another non-targeted anatomic region can be unintentionally stimulated by errant signals transmitted by the stimulated vagus nerve 10, causing pain or discomfort in the non-targeted anatomic region. A second set (or blocking set) of electrodes (not shown), but similar to the electrodes 140, can be placed between the vagus nerve 10 and the non-targeted anatomic region for blocking the errant signals. The second set of electrodes can also be placed in a different location about the vagus nerve, but in the path from the vagus nerve to the non-targeted anatomic region. The second set of electrodes can transmit a second or blocking signal simultaneously with the first signal, such that the second signal interferes with and cancels or blocks the transmission of the errand signals from the vagus nerve 10 to the non-targeted region. The transmission of the second signal can be synchronized to coincide with the transmission of the first signal, so that beneficial signals from the vagus nerve 10 during the off time of the first stimulation signal are not blocked by the second signal. In one embodiment, both the first set of electrodes 140 for the therapy signal and the second set of electrodes 140 for the blocking signal can be electrodes with sharp tips 142. In another embodiment, only the second set of electrodes for the blocking signal include with sharp tips 142. It will be also appreciated that the therapy electrodes and the blocking electrodes can be included in a single implantable device 120 or in separate implantable devices.

In various embodiments, although the starting voltage can be very high and the peak current very large, the duration of the pulse is very brief. The small amount of energy applied per pulse to the nerve tissue tends to allow the nerve tissue recover more readily from the effects of stimulation. Further, using pointed electrodes 140, as described herein can limit tissue stress to a very small area of the nerve, allowing the tissue to recover more quickly and enabling electroporation.

Additionally, although certain embodiments, stimulation signals and therapy protocols may be described in connection to specific tissue sites, as the vagus nerve or the spinal cord or particular vertebrae, it should be understood that the present teachings are applicable to any tissue site, neuron fiber, neuron bundle or spinal cord site. Further, the present teaching can be applied to transmit stimulation signals for therapy function and/or stimulation signals for blocking function, as described above.

The foregoing discussion discloses and describes merely exemplary arrangements of the present teachings. Furthermore, the mixing and matching of features, elements and/or functions between various embodiments is expressly contemplated herein, so that one of ordinary skill in the art would appreciate from this disclosure that features, elements and/or functions of one embodiment may be incorporated into another embodiment as appropriate, unless described otherwise above. Moreover, many modifications may be made to adapt a particular situation or material to the present teachings without departing from the essential scope thereof. One skilled in the art will readily recognize from such discussion, and from the accompanying drawings and claims, that various changes, modifications and variations can be made therein without departing from the spirit and scope of the present teachings as defined in the following claims.

What is claimed is:

1. An implantable medical device comprising:
   an implantable device including a processor and a pulse generator;
   a first lead having first and second ends, the first end of the lead operably and conductively coupled to the implantable device;
   a first electrode operably and conductively coupled to the second end of the first lead, the first electrode having a first sharp tip for transmitting and focusing a stimulation signal from the pulse generator to a tissue site;
   a discrete nonconductive barrier not integrally formed on the first sharp tip, said barrier having a major axis extending perpendicularly from a major axis of the first electrode, wherein said barrier is positionable between the first sharp tip and tissue, the barrier having a thickness capable of protecting the tissue from mechanical damage and capable of allowing the stimulation signal therethrough,
   wherein the barrier includes at least one through passage in a vicinity of the first sharp tip.

2. The medical device of claim 1, further comprising a second lead having first and second ends, the first end of the second lead operably and conductively coupled to the implantable device; and
   a second electrode operably and conductively coupled to the second end of the second lead.

3. The medical device of claim 2, wherein the second electrode has a second sharp tip.

4. The medical device of claim 1, wherein the stimulation signal is high voltage and very brief duration.

5. The medical device of claim 1, wherein the tissue site is adjacent a vagus nerve.

6. The medical device of claim 1, wherein the tissue site is adjacent a spinal cord.

7. A medical device comprising:
   an implantable device including a pulse generator; and
   a plurality of electrodes operably and conductively coupled to the implantable device, at least a first electrode of the plurality electrodes having a sharp tip;
   a discrete nonconductive barrier not integrally formed on the sham tip, said barrier having a major axis extending perpendicularly from a major axis of the at least one electrode, wherein said barrier is positionable between the sharp tip and tissue, the barrier comprising a passage therethrough to allow direct passage of a stimulation signal from the pulse generator to a tissue site.

8. The medical device of claim 7, wherein each electrode of the plurality of electrodes includes a sharp tip and wherein the plurality of electrodes including the first electrode is arranged in a plurality of opposing pairs, each pair operably positionable on opposite sides of a nerve or tissue.

9. The medical device of claim 7, wherein the plurality of electrodes including the first electrode is arranged in a pair of opposing comb-like electrode structures.

10. The medical device of claim 7, wherein the plurality of electrodes includes a second electrode having a sharp tip.

11. The medical device of claim 10, wherein the first and second electrodes are operably positionable on opposite sides of tissue.

12. The medical device of claim 10, wherein the first and second electrodes are operably positionable on a same side of tissue.

13. The medical device of claim 10, further comprising first and second discrete nonconductive barriers not integrally formed on the sharp tips of the first and second electrodes, said barriers having a major axis extending perpendicularly from a major axis of the first and second electrodes and operably positionable respectively between the first and second electrodes and the tissue.

14. A method of delivering tissue stimulation comprising:
   generating an electrical stimulation signal from a signal generator of an implantable medical device;
   coupling a first electrode having a first sharp tip to the signal generator of the implantable medical device
   positioning a discrete insulative barrier between the first sharp tip of the first electrode and tissue;
   positioning the first sharp tip of the first electrode adjacent the discrete insulative barrier, the discrete insulative barrier not integrally formed on the first sharp tip, said barrier having a major axis extending perpendicularly from a major axis of the first electrode, wherein the barrier includes a passage therethrough; and
   transmitting the electrical stimulation signal from the first sharp tip through the passage directly into tissue adjacent the insulative barrier.

15. The method of claim 14, wherein positioning the first sharp tip of the first electrode includes positioning the first sharp tip in direct contact with the discrete insulative barrier, and the barrier in direct contact with the tissue.

16. The method of claim 14, further comprising:
positioning a second sharp tip of a second electrode in contact with tissue, the second electrode conductively and operably coupled to the implantable medical device; and
transmitting the signal through the second sharp tip.

17. The method of claim 16, further comprising positioning the first and second sharp tips on opposite sides of tissue.

18. The method of claim 16, wherein the signal is a high voltage very brief duration pulse.

19. The method of claim 18, wherein the voltage is in a range of about 1 kV to about 10 kV and the duration is in a range of about 10 ns to about 1000 ns.

20. The method of claim 16, further comprising inducing an electric field in the tissue, the electric field localized in a vicinity of the first and second sharp tips.

21. The method of claim 16, wherein the signal is a transmitted through the tissue between the first and second sharp tips.

22. The method of claim 14, wherein the signal includes repeated pulses at a first therapy stimulation level characterized by one of voltage level, duration, and number of electrodes delivering stimulation and repeated pulses at a second therapy stimulation level reduced from the first therapy stimulation level.

23. The method of claim 14, wherein transmitting the signal to the tissue through the first sharp tip includes transmitting therapeutic stimulation.

24. The method of claim 14, wherein transmitting the signal to the tissue through the first sharp tip includes transmitting blocking stimulation.

25. An implantable medical device comprising:
an implantable device including a processor and a pulse generator;
a first lead having first and second ends, the first end of the lead operably and conductively coupled to the implantable device;
a first electrode operably and conductively coupled to the second end of the first lead, the first electrode having a first sharp tip for transmitting and focusing a high voltage stimulation signal from the pulse generator to a tissue site, the voltage is in a range of about 1 kV to about 10 kV and the duration is in a range of about 10 ns to about 1000 ns;
a discrete nonconductive barrier not integrally formed on the first sharp tip, said barrier having a major axis extending perpendicularly from a major axis of the first electrode, wherein said barrier is and positionable between the first sharp tip and tissue, the barrier having a thickness capable of protecting the tissue from mechanical damage and capable of allowing the stimulation signal therethrough,
wherein the barrier includes at least one through passage in a vicinity of the first sharp tip.

* * * * *